United States Patent [19]

Apicella

[11] Patent Number: 4,859,421
[45] Date of Patent: Aug. 22, 1989

[54] DISPOSABLE ANTIGEN CONCENTRATOR AND DETECTOR

[75] Inventor: Michael A. Apicella, North Tonawanda, N.Y.

[73] Assignee: The Research Foundation of State University of New York, Albany, N.Y.

[21] Appl. No.: 65,424

[22] Filed: Jun. 23, 1987

[51] Int. Cl.⁴ ............................................. G01N 31/22
[52] U.S. Cl. ........................................ 422/61; 422/58; 436/808; 436/809; 436/526; 435/291
[58] Field of Search .................... 422/61, 58; 435/291; 436/807, 808, 809, 526

[56] References Cited

U.S. PATENT DOCUMENTS

| | | | |
|---|---|---|---|
| Re. 29,725 | 8/1978 | Johnson et al. | 23/230 R |
| 3,074,544 | 1/1963 | Bollmeier et al. | 206/47 |
| 3,540,857 | 11/1970 | Martin | 422/61 |
| 3,554,705 | 1/1971 | Johnston et al. | 23/253 |
| 3,582,283 | 6/1971 | Mirasol, Jr. | 23/253 |
| 3,726,645 | 4/1973 | Kaczmarek | 422/61 |
| 3,740,196 | 6/1973 | Stroternoff | 422/61 |
| 3,748,098 | 7/1973 | Dutch | 422/61 |
| 3,835,834 | 9/1974 | Brown et al. | 128/2 W |
| 3,847,279 | 11/1974 | Montgomery | 206/219 |
| 3,964,604 | 6/1976 | Prenntzell | 206/219 |
| 3,981,981 | 9/1976 | Reunanen | 424/1.5 |
| 3,986,834 | 10/1976 | Steinbrink, Jr. | 23/230 B |
| 4,081,077 | 3/1978 | Franck | 206/219 |
| 4,162,003 | 7/1979 | Bartos et al. | 206/219 |
| 4,239,853 | 12/1980 | Bradley | 422/61 |
| 4,276,051 | 6/1981 | Ginsburg et al. | 436/47 |
| 4,308,347 | 12/1981 | Forrer et al. | 435/34 |
| 4,541,987 | 9/1985 | Guadagno | 422/61 |
| 4,582,685 | 4/1986 | Guadagno et al. | 422/61 |
| 4,643,973 | 2/1987 | Avery | 422/58 |
| 4,673,657 | 6/1987 | Christian | 422/58 |
| 4,690,801 | 9/1987 | Anderson | 436/45 |

Primary Examiner—Michael S. Marcus
Assistant Examiner—Lyle Alfandary Alexander
Attorney, Agent, or Firm—Robert P. Simpson; Michael L. Dunn

[57] ABSTRACT

The present invention relates to a disposable test kit which contains selected reactants, or reagents, necessary for the rapid concentration and detection of selected antigens from biologic extracts. Typically, and preferably, the time required for concentration and detection is less than one hour. The present kit includes internal false position and false negative controls and suitably has a standard color code to assist in the interpretation of the test results. The present kit is a unitary, compartmented package having a reaction chamber, preferably centrally located thereon, and at least one reagent storage chamber. Each reagent storage chamber is connected to the reaction chamber through a valve means which allows fluid flow from the reagent chamber to the reaction chamber, but inhibits flow from the reaction chamber to the reagent chamber. The top portions of the reagent chambers are fabricated of a flexible, or pliable, material, preferably transparent or semi-transparent. Manual pressure applied to the top portion of a reagent chamber causes the contents of the reagent chamber to be controllably transferred through the valve means to the reaction chamber.

5 Claims, 1 Drawing Sheet

DISPOSABLE ANTIGEN CONCENTRATOR AND DETECTOR

This invention was made with Government support under National Institute of Health Grant No. R01 AI18384.

BACKGROUND OF THE INVENTION

The present invention relates to a self-contained, disposable diagnostic assay device, or kit, that is particularly useful in field locations, that is, locations distant from formal detection, or analytical, facilities. The present test kit is eminently useful in the concentration and the subsequent detection of antigens using appropriate antibody reactant systems and colorimetric reagents. The present invention is particuarly suited to use in the areas of human and veterinary medicine, biologic testing of water, and industrial effluent testing.

Although the present kit is particularly suited to use under the supervision of a person having knowledge and experience in the analytical field, it has equally wide application in the area of tests conducted by laymen and is particularly useful in the area of self-administered, or private, tests. In the latter cases, the reagents, or reactants, utilized in the kit are suitably selected to be safe under such conditions of use.

The present kit is particularly useful in the concentration and detection of selected antigens from biologic extracts by exposure of the extract to selected reactants, or reagents, typically antigens or antibodies, and subsequently identifying the presence of specific antigens by colorimetric means. Antibodies are frequently produced as a defense reaction when foreign substances are taken in, parenterally, by living bodies. Substances which produce antibodies are known as antigens. Typically, antigens are mixtures of proteins, protein degradation products, lipids and polysaccharides, and include, for example, bacteria, viruses, blood corpuscles and toxins. The antibodies formed bind to the antigens by a highly specific reaction. Because of such high degree of specificity, antibodies can be utilized to identify the corresponding antigens. If the presence of certain antibodies can be demonstrated in the biologic extract from an organism, it can be concluded with a high degree of certainty that the organism has at some time been exposed to the corresponding antigen. While the methods of detecting antibodies vary, they commonly comprise the step of bringing a biologic fluid, for example blood, into contact with a selected antigen. If an antigen-antibody reaction takes place, this is evidence for the presence of the corresponding antibody. It is also evidence that there has been an exposure to antigens when the corresponding antibodies are present in the sample even if the antigens are no longer present in the sample.

Various analytic or testing devices, some of which rely on antigen/antibody reactions, have been previously proposed for testing biological extracts. The most pertinent prior art relevant to the present invention presently known to applicant is as follows. U.S. Pat. No. 3,981,981 teaches a reaction vessel utilized to detect specific antigens. U.S. Pat. No. 4,081,077 discloses a compartmented package having a peelable cover and a mixing chamber. U.S. Pat. No. 4,582,685 relates to a portable test kit for performing medical tests in the field using a chemical test pad. U.S. Pat. No. Re. 29,725 teaches a multi-compartmented biomedical testing container for field use. U.S. Pat. No. 4,162,003 discloses a disposable serological test kit which may include a spot plate. U.S. Pat. No. 3,582,283 relates to a disposable test kit having a plurality of reagent storage chambers connecting to a reaction body chamber which is useful for testing fluids. U.S. Pat. No. 3,554,705 teaches a similar disposable test kit in which the reaction chamber is also useful as a cuvette for optical analysis. U.S. Pat. No. 3,835,834 relates to a disposable culture transporting device containing a culture medium. U.S. Pat. No. 3,986,834 teaches a kit for testing biological fluids wherein a standard test is conducted simultaneously with a probative test.

BRIEF DESCRIPTION OF THE INVENTION

The present invention relates to a disposable test kit which contains selected reactants, or reagents, necessary for the rapid concentration and detection of selected antigens from biologic extracts. Typically, and preferably, the time required for concentration and detection is less than one hour. The present kit includes internal false positive and false negative controls and suitably has a standard color code to assist in the interpretation of the test results.

The present kit is a unitary, compartmented package having a reaction chamber, preferably centrally located thereon, and at least one reagent storage chamber. Each reagent storage chamber is connected to the reaction chamber through a valve means which allows fluid flow from the reagent chamber to the reaction chamber, but inhibits flow from the reaction chamber to the reagent chamber. The top portions of the reagent chambers are fabricated of a flexible, or pliable, material, preferably transparent or semi-transparent. Manual pressure applied to the top portion of a reagent chamber causes the contents of the reagent chamber to be controllably transferred through the valve means to the reaction chamber.

The base portion of the reaction chamber contains a positive and a negative control means. The control means is comprised of small amounts of chemical reactants, typically in the form of discs, separated from the remainder of the reaction chamber base portion by chemically inert partitions or by blocking, e.g. treating the substrate area beneath the test spot with a nonspecific binding protein. The chemical reactants in the control means react with the reagent materials giving both a visual positive test and a visual negative test. If either control test fails, the operator is put on notice that the main, or primary, analysis may be in question.

DETAILED DESCRIPTION OF THE INVENTION

The present invention will now be described in greater detail by reference to the accompanying drawings in which similar components are identified by similar numbers in each of the views.

Figure 1:
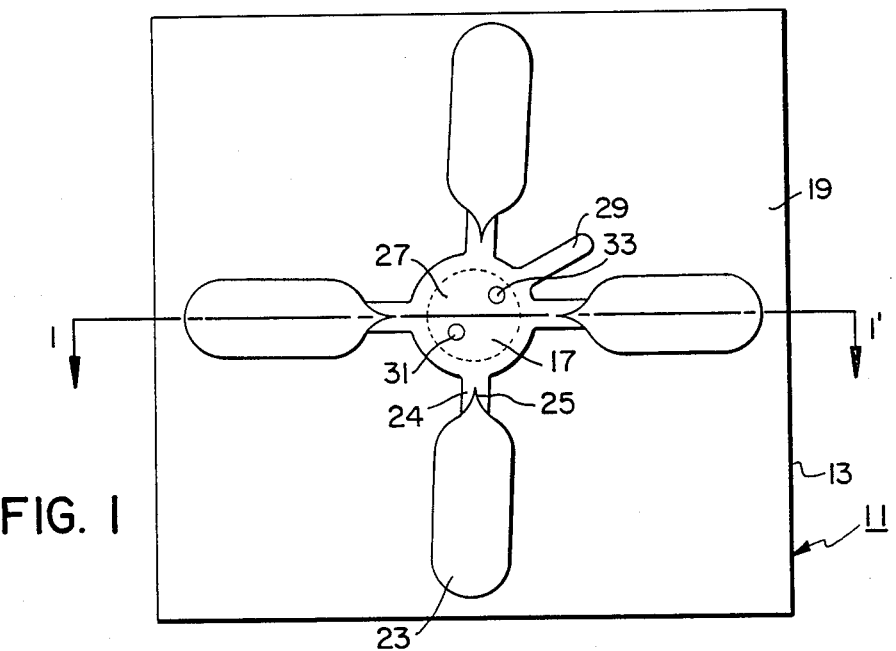
FIG. 1 is a top planar view of one embodiment of a test kit of the present invention.

Looking now at FIG. 1, the present diagnostic assay kit is comprised of a unitary, compartmented package, generally denoted as 11. As shown, package 11 is generally rectangular, however, it will be understood that other shapes may be employed with equal utility. Typically, package 11 ranges in linear size from about two inches by two inches to about six inches by six inches.

Suitably, a size of about four inches by four inches is aptly used.

Package 11 has a rigid or semirigid base member, or portion, 13 having a compartmented reaction chamber 17. Preferably, reaction chamber 17 is a cavity, or depressed portion, such as 15, formed in base member 13. Base member 13 is preferably fabricated of a rigid or semi-rigid material. At least the surface area of the reaction chamber and other areas on base member 13 which will be exposed to reagents or reactants are fabricated of a impervious, chemical resistant material, for example, polyethylene or polypropylene. Suitably, base member 13 is fabricated of a laminate having a cardboard bottom, or center, portion and a chemical resistant top, or surface, portion. Cavity 15 may be easily formed by forming an appropriate depression in the base member by a molding operation. The entire base member 13 may suitably be formed by injection molding.

The size and shape of cavity 15, which preferably forms reaction chamber 17, is not critical. Although generally circular or elliptical shapes are preferred, other shapes, for example square or rectangular, are also useful.

Package 11 has a cover member 19. Cover member 19 has at least one outward extending protrusion, such as 21 forming the top portion of a reagent chamber. At least the protruded portions of cover member 19 are fabricated of a flexible or pliable material, for example, polyethylene or polypropylene, preferably transparent or semi-transparent. Although opaque materials, such as metal or foil, may be utilized in the cover member, they are not preferred as the contents of reagents housed in the protruded portions and cannot be visually determined.

Cover member 19 is positioned on base member 13 to form at least one, and typically a plurality of, reagent chambers, such as 23. Reagent chambers 23 are connected to reaction chamber 17 by valve means 25 either directly or through covered channels, such as 24. Valve means 25 allows liquid flow from reagent chambers, such as, 23, into reaction chamber 17 and prevents flow from the reaction chamber to the reagent chambers. Suitably, valve means 25 is a plastic flap anti-backflow valve. Alternatively, and more economically, valve means 25 may be fabricated as a constriction in covered channel 24 that is sealed, suitably by heat sealing, to base member 13. Upon the application of pressure to the outside of reagent chamber 23, the seal is broken and reagent flow initiated and upon release of pressure, tension closes the channel connection.

Reagent chambers, such as 23, are at least partially compressible. Preferably, the top portion of reagent chambers, such as 23, are formed of flexible protruded portions of cover member 19. Manual pressure applied to the top of reagent chambers, such as 23, compresses chamber 23 and forces, in a controllable manner, the material stored in the reagent chamber to pass through valve means 25 into reaction chamber 17.

Until use reaction chamber 17 is sealed in an impermeable, air-tight manner by a cover, such as 27. Appropriately, a portion of cover member 19 may also provide reaction chamber cover 27. Reaction chamber cover 27 is opened, or unsealed, to allow a sample to be placed in the reaction chamber suitably by a tab, or grip, such as 29.

The present kit includes a positive control means, for example, disc 31, and a negative control means, for example, disc 33 located in reaction chamber 17. Discs 31 and 33 are preferably separately housed in open top compartments maintained physically and chemically apart from the remainder of reaction chamber 17. Discs 31 and 33 are comprised of reactants which coreact with reagents or by products of the reagents utilized in the test to be carried out. The positive and negative control means are selected to visually indicate that the reagent, or reagents, have not aged, oxidized or otherwise been adversely affected by storage or by the current and actual test conditions.

In use reaction chamber cover 27 is removed exposing reaction chamber 17. The biologic sample to be tested, for example, blood, urine, cerebrospinal fluid, abscess fluid, pleural fluid for specific antigens (bacterial, tumor or hormones) waste materials, or water supplies, is placed in reaction chamber 17. The reagent chambers 23 contain an appropriate reagent which is controllably transferred to the reaction chamber 17 by manual pressure, or squeezing, the flexible top portions of reagent chambers 23. The positive and negative test discs 31 and 33 are observed. If both tests are favorable, the primary, or main, assay or analysis is observed. Suitably, the primary assay, or analysis, is conditioned on a colorimetric determination and a colorimetric standard may be suitably positioned on the body of the kit.

The assay, or analysis, may be easily adapted to various systems, known in the art, for collecting and determining antigens from biologic extracts. For example, the surface of reaction chamber 17 may be untreated nitrocellulose, in which case it is suited to use in either a direct assay, or as a capture system wherein the antibody is bound directly to the surface of the reaction system. The present kit may be adapted to an affinity system by the utilization of a magnetized vinyl surface in the reaction chamber and the inclusion of antibody coated, typically latex, magnetic beads. In use, the practical volumes of samples may be as small as 0.2 ml (for example, cerebrospinal fluid in direct assay) or as large as 1000 ml samples in a system using antibody coated magnetic beads.

The present invention will now be described more in detail by reference to the following example which is to be interpreted as illustrative and not limiting.

EXAMPLE

Figure 2:
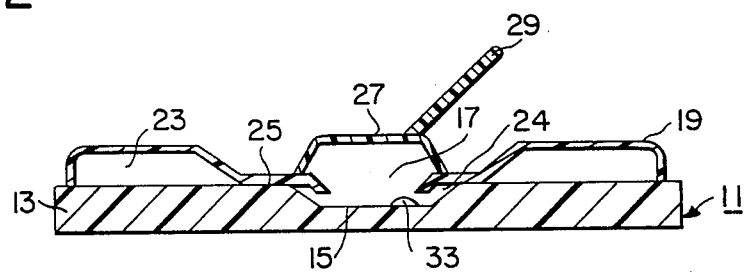
FIG. 2 is a side planar sectional view of the kit shown in FIG. 1 taken along lines 1 and 1'.

An embodiment of the present kit having reagent chambers, similar to that shown in FIGS. 1 and 2 was used to analyze a sample of about 0.2 ml of spinal fluid from a febrile two year old child. The base of the reaction chamber was provided with a surface of nitrocellulose. The reagents used in each of the reagent chambers were sterile. The kit, including the reagent chambers, was previously sterilized and the reagent chambers were filled under sterile conditions. The volume of reagent in each chamber was about 0.5 ml. The first reagent chamber, Chamber A, contained 3% skimmed milk, which was subsequently utilized to block unbound sites on the nitrocellulose substrate after reaction with the spinal fluid sample. The second reagent chamber, Chamber B, contained a solution of murine monoclonal IgG antibodies against the capsular polysaccharides of the bacterial organisms which commonly cause meningitis in young children (meningococcus A, B and C, Haemophilus influenzae type b, and Str. pneumonia). The third chamber, Chamber C, contained a solution of peroxidase labelled antimurine IgG conjugate antibody. The fourth chamber, Chamber D, contained a solution of a substrate to the visual detection of the bound enzyme-antibody conjugate. The nitrocellulose surface in the reaction chamber was provided with a positive control comprised of a 0.5 cm diameter spot containing the representative capsular polysaccharides. The spot was blocked in order that no other antigens could adhere to the nitrocellulose layer beneath by treating the test spot area with a non-specific binding protein. As further explained below, the positive test spot, in the present example, must be blue at the end of the analysis. The nitrocellulose layer was provided with a negative control comprised of an additional 0.5 cm diameter spot which contained none of the representative capsular polysaccharides. The negative control area is also blocked to prevent any antigens from adhering to the nitrocellulose layer beneath. As explained further below, the negative control in this example must be white at the end of the analysis.

The analysis was carried out by removing the kit cover and applying the spinal fluid sample to the layer of nirrocellulose in the base of the reaction chamber. The applied spinal fluid sample was allowed to stand for a period of five minutes. The nitrocellulose surface of the reaction chamber was then washed with a buffered saline solution. The outside portion of Chamber A was then compressed and the contents of the chamber forced into the reaction chamber. The reactants were allowed to stand for a period of ten minutes and the reaction chamber surface again washed with buffered saline. The contents of Chamber B were then discharged into the reaction chamber and maintained at 37° C. for a period of 15 minutes. The reaction chamber surface was again washed with a buffered saline solution. The contents of Chamber C were then added to the reaction chamber and this maintained at 37° C. for 15 minutes. The nitrocellulose surface in the reaction chamber was then again rinsed with buffered saline. The contents of Chamber D were then added to the reaction chamber and allowed to stand at room temperature. Within minutes a blue color developed over the reaction chamber surface, including the positive control area. The blue color indicated the presence of bacterial capsular polysaccharide in the spinal fluid sample and a diagnosis of bacterial meningitis in the patient was made. The area over the negative control must remain white for the test to be positively interpreted and the diagnosis made.

The theory and logic of the present analysis example may be explained as follows: the nitrocellulose surface on the reaction chamber binds any bacterial antigens that may be present in the spinal fluid samples. The skimmed milk serves to block all sites on the nitrocellulose to which the spinal fluid antigens failed to bind preventing any protein in subsequently used reagents from non-specifically binding and thereby causing a false positive test. The antibodies in Chamber B give specificity to the test by binding only to the appropriate bacterial antigens. The only specific antibodies that would be bound at this point are those bound in conjunction with the appropriate bacterial antigens. In turn, when the enzyme conjugate antibody reagent from Chamber C is added, the only enzyme-antibody-conjugate present will be the conjugate associated with the specific antibody antigen on the nitrocellulose layer. An appropriately selected enzyme substrate is then added from Chamber D and an appropriate color will develop only in association with the specific enzyme-antibody-conjugate-specific antibody-antigen.

While preferred embodiments of the invention have been described herein, it is obvious that omissions, changes, and additions may be made in such embodiments without departing from the spirit and scope of the invention.

What is claimed is:

1. A disposable analytical test kit capable of being handheld comprised of:
   (a) a base member,
   (b) a reaction chamber, having a chemically inert surface, positioned in said base member, said reaction chamber having a removable cover for directly entering a sample to be tested into said reception chamber,
   (c) at least one reagent chamber, having a chemically inert surface, positioned on said base member, each of said reagent chambers having separate, manually compressible top portions,
   (d) each of said reagent chambers connected to said reaction chamber by a separate anti-back flow valve means, each of said valve means constructed to allow flow from a selected reagent chamber by the direct application of manual pressure on the top portion of said selected reagent chamber, into said reaction chamber and to prevent flow from said reaction chamber into said respective reagent chamber, and
   (e) said reaction chamber having separate positive and negative control means in the base portion thereof, said control means visually indicating a positive and a negative test of reagents or reactions introduced or taking place in said reaction chamber.

2. The test kit of claim 1 wherein said inert surface in said reaction chamber is nitrocellulose.

3. The test kit of claim 1 wherein said inert surface in said reaction chamber is magnetized vinyl.

4. The test kit of claim 3 wherein the reaction chamber contains antibody coated beads.

5. The teat kit of claim 1 wherein the said control means is comprised of color comparison patches.

* * * * *